United States Patent [19]

Jenkins

[11] 4,391,599
[45] Jul. 5, 1983

[54] APPARATUS FOR PROVIDING A CONTROLLED FLOW OF INTRAVENOUS FLUID TO A PATIENT

[75] Inventor: Jon A. Jenkins, Rancho Santa Fe, Calif.

[73] Assignee: IMED Corporation, San Diego, Calif.

[21] Appl. No.: 274,154

[22] Filed: Jun. 16, 1981

Related U.S. Application Data

[63] Continuation of Ser. No. 4,464, Jan. 18, 1979, abandoned.

[51] Int. Cl.³ ............................................... A61M 5/00
[52] U.S. Cl. .................................... 604/118; 604/126; 604/152
[58] Field of Search ........... 128/214 R, 214 E, 214 F, 128/214.2, 230, 273, DIG. 12, DIG. 13; 417/38, 43, 63, 435; 604/118, 122, 126, 152

[56] References Cited

U.S. PATENT DOCUMENTS

| | | | |
|---|---|---|---|
| 2,625,933 | 1/1953 | Salisbury | 128/214.2 |
| 2,927,582 | 3/1960 | Berkman et al. | 128/DIG. 3 |
| 3,091,239 | 5/1963 | Moeller | 128/214 F |
| 3,543,752 | 12/1970 | Hesse et al. | 128/214 E |
| 3,901,231 | 8/1975 | Olson | 128/214 F |
| 3,985,133 | 10/1976 | Jenkins et al. | 128/214 F |

FOREIGN PATENT DOCUMENTS 2371202 7/1978 France .......................... 128/214 F

*Primary Examiner*—Dalton L. Truluck
*Attorney, Agent, or Firm*—Ellsworth R. Roston; Charles H. Schwartz

[57] ABSTRACT

Apparatus provides a controlled flow of fluid at particular rates from a source to a patient at controlled pressures of low value. The apparatus includes an input line connected to the source. An output line extends to the patient and implementing means such as a pump implements the flow of fluid from the input line to the output line at a particular rate. The source is disposed a particular distance above the implementing means to produce a particular pressure of the fluid at the implementing means and to provide this particular pressure to the fluid flowing to the patient.

A bypass line is connected across the implementing means. Means in the bypass line, such as a chamber and a flexible diaphragm in the chamber, isolate the input side of the bypass line against the flow of fluid to the output side of the bypass line.

Hydrophilic membrane means may be provided between the bypass line and the implementing means to provide for a passage of fluid from the input line to the bypass line and to prevent a passage of air bubbles from the bypass line to the input line. Hydrophilic membrane means may also be provided between the output line and the bypass line for similar purposes.

Means may be disposed in the output side of the bypass line to sense the presence of liquid. Such sensing of liquid indicates a pressure of fluid in the output line greater than the pressure of the fluid in the input line at the position of the implementing means. This may result from an obstruction in the output line or an improper operation of the implementing means. When the sensing means becomes operative, the operation of the implementing means is discontinued and aural and/or visual alarms are energized.

16 Claims, 4 Drawing Figures

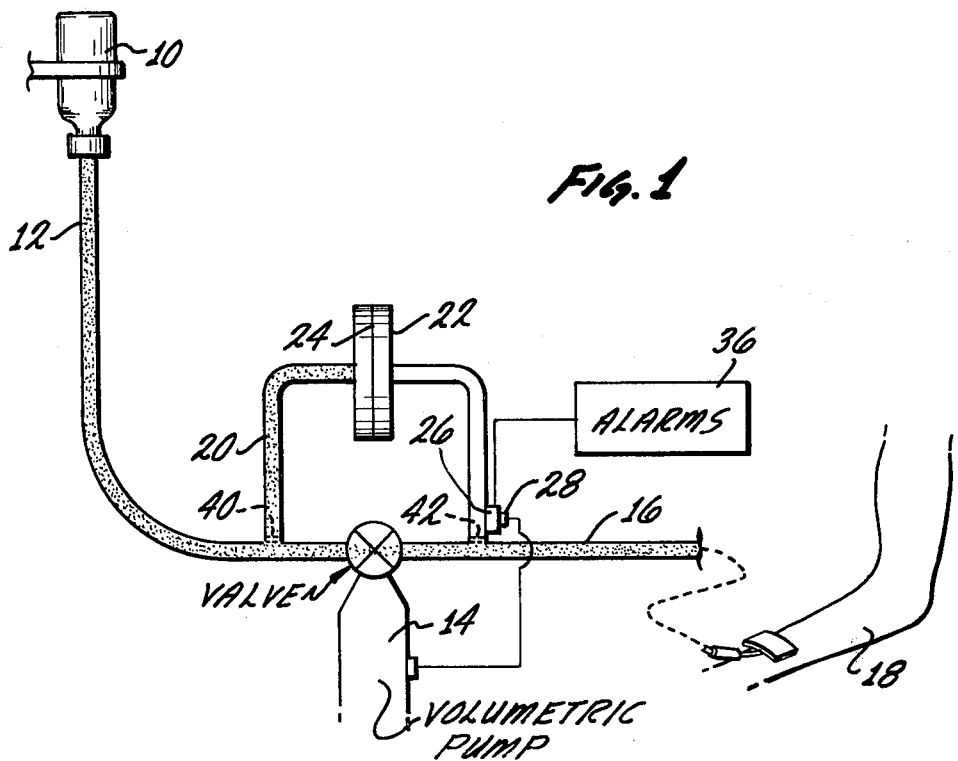
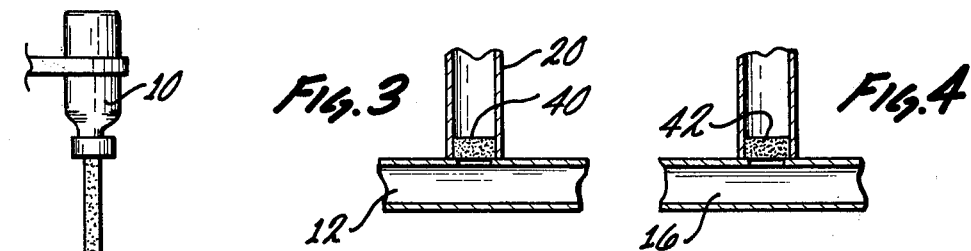
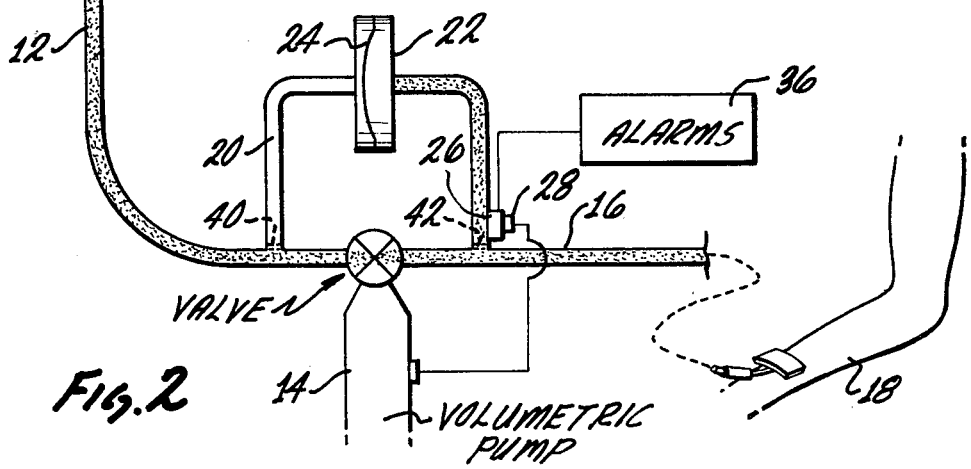

APPARATUS FOR PROVIDING A CONTROLLED FLOW OF INTRAVENOUS FLUID TO A PATIENT

This is a continuation of application Ser. No. 4,464 filed Jan. 18, 1979, now abandoned.

This invention relates to apparatus for introducing fluids such as intravenous fluids to a patient. More particularly, the invention relates to apparatus for introducing controlled amounts of fluid at preselected rates to a patient under fail-safe conditions where the introduction of the fluid is interrupted if the pump becomes inoperative or an obstruction occurs in the output line to the patient. The invention is also advantageous because it is able to introduce intravenous fluids to a patient at low pressures.

As medical technology becomes advanced, it becomes increasingly apparent that the care of patients after surgery or in advanced stages of illness is quite sensitive and requires the imposition of different parameters for each individual patient. For example, after surgery, each individual patient requires the introduction of different amounts of fluid at preselected rates in accordance with a number of parameters unique to each patient. These parameters include the sex, age, weight and physical condition of the patient.

Considerable advances have been made in apparatus for providing for the introduction of controlled amounts of fluid to a patient at preselected rates. For example, in U.S. Pat. No. 3,985,133 issued to me on Oct. 12, 1976, and assigned of record to the assignee of record of this application, a volumetric pump is disclosed and claimed for introducing a controlled amount of fluid to a patient at a preselected rate. Similarly, in copending application Ser. No. 913,294 filed by me on June 7, 1978, and assigned of record to the assignee of record of this application, a controller is disclosed and claimed for providing for the flow of fluid on a gravitational basis to a patient at a preselected rate.

This invention provides apparatus which includes a pump for introducing fluid to a patient at a preselected rate. The pump may be a volumetric pump but other types of pumps may be used. However, the apparatus provides the intravenous fluid to the patient at a particular pressure which is independent of the pressure produced by the pump. This particular pressure is dependent upon the height of the source of the intravenous fluid above the pump. When an obstruction occurs in the output line or the operation of the pump becomes defective, the pressure of the fluid in the output line increases above the particular pressure. This causes a sensor to be energized for discontinuing the operation of the pump. In this way, the apparatus provides the advantages of a pump and a controller in providing the flow of fluid at a particular rate like a pump but providing the flow of fluid at a low pressure like a controller.

The apparatus includes an input line connected to a source, an output line extending to the patient and implementing means such as a pump connected between the input and output sides of the bypass line. The source is disposed a particular distance above the implementing means to produce a particular pressure of the fluid at the implementing means in accordance with this distance. This particular pressure controls the pressure of the fluid introduced to the patient.

A bypass line is connected across the implementing means. Means in the bypass line isolate the input side of the bypass line against the flow of fluid to the output side of the output line. Such means may include a chamber and a resilient diaphragm disposed in the chamber to block the passage of fluid through the chamber.

Hydrophilic membrane means may be provided between the bypass line and the implementing means to provide for a passage of a fluid such as intravenous fluid from the input line to the bypass line and to prevent a passage of air bubbles from the bypass line to the input line. Hydrophilic membrane means may also be provided between the output line and the bypass line for similar purposes.

Sensing means may be disposed adjacent the output side of the bypass line to sense the presence of fluid at the particular position. The sensing of fluid in the bypass line indicates a pressure of fluid in the output line greater than the pressure of fluid in the input line at the implementing means. This pressure of fluid in the output line may result from an obstruction in the output line or an improper operation of the implementing means such as the pump. When the sensing means becomes operative, the operation of the implementing means such as the pump is discontinued and alarms are initiated.

In this way, the apparatus introduces fluid to the patient at a controlled rate dependent upon the operation of the pump. However, the fluid is introduced to the patient at a relatively low pressure dependent upon the distance of the source above the pump. This pressure may be controlled at low levels by adjusting the distance of the source above the pump. The apparatus accordingly has the advantages of a pump in providing the flow of fluid at controlled rates and the advantages of a controller in providing the flow of fluid at low pressures. The apparatus is also fail-safe in becoming inoperative when the pressure of the fluid in the output line exceeds a particular pressure dependent upon the distance of the source above the implementing means such as the pump.

In the drawings:

FIG. 1 is a schematic diagram of an electrical and hydraulic system constituting one embodiment of the invention and schematically illustrates the normal operation of the system;

FIG. 2 is a schematic diagram of the embodiment shown in FIG. 1 and illustrates the condition of the system when an obstruction occurs in a line introducing fluid to a patient; and FIGS. 3 and 4 are enlarged fragmentary drawings of portions of input and output sides of the system shown in FIGS. 1 and 2.

In the embodiment of the invention shown in FIG. 1, a source 10 of a fluid such as an intravenous fluid is provided. The source 10 is preferably disposed at an elevated level. An input line 12 extends from the source 10 to an elevation at a particular distance below the source 10. In this way, a pressure exists in the fluid at the output end of the input line, this pressure being dependent upon the difference in elevation between the source 10 and the output end of the input line.

Implementing means are connected to the output end of the input line 12 to provide for the flow of fluid to the patient. The implementing means may be a pump 14. A suitable pump is disclosed and claimed in U.S. Pat. No. 3,985,133 issued to me on Oct. 12, 1976, for an IV PUMP and assigned of record to the assignee of record of this application. This pump constitutes a volumetric pump. However, other types of pumps than volumetric pumps may also be used.

The input side of an output line 16 is connected to the pump 14 and the output side of the output line is connected to a patient 18. The input side of the output line 16 is disposed above the patient so that a back pressure will be produced in the line 16 when an occlusion occurs in the line. This back pressure is dependent upon the height of the input side of the output line 16 above the patient 18.

A bypass line 20 is connected between opposite ends of the pump 14. Isolating means are disposed in the bypass line 20 to inhibit the flow of fluid through the bypass line between the input line 12 and the output line 16. The isolating means may include a chamber 22 and a resilient diaphragm 24 extended across the chamber.

A sensor 26 is disposed adjacent the bypass line 20 at a position on the output side of the pump 14. The sensor 26 is preferably disposed at a position above the output line 16 so that it will become operative only when fluid has risen in the output line to the position of juncture with the bypass line 20 and then has risen in the bypass line to the particular position. The sensor 26 may be constructed in a conventional manner. For example, the sensor may be constructed to detect changes in the amount of light passing through the bypass line when the fluid rises to the particular level in the bypass line 20.

In the normal operation of the apparatus constituting this invention, the pump 14 operates to implement the flow of fluid from the source 10 to the patient at a rate dependent upon the setting of the pump. Fluid does not flow through the bypass line because of the inclusion of the diaphragm 24.

Since the source 10 is above the pump 14, the pressure of the fluid at the input end of the pump is at an elevated level. This causes the diaphragm 24 to be flexed toward the right in FIG. 1 during the time that no build-up of the fluid occurs in the output line 16. This flexing of the diaphragm 24 helps to alleviate the pressure in the output line.

Occasionally, an occlusion may occur in the output line 16 or the pump 14 may become defective. Under such circumstances, fluid may accumulate in the output line 16 and produce a back pressure in the line. This back pressure is produced because the input side of the output line 16 is disposed above the patient.

As the fluid in the output line 16 rises, the diaphragm 24 is flexed to the left to alleviate the pressure on the diaphragm. This is illustrated schematically in FIG. 2. When the fluid has risen to the level of the sensor 26, the sensor 26 is operated. This in turn causes a switch 28 associated with the sensor 26 to become opened so that the circuit to the pump 14 is interrupted. When the sensor 26 is operated, alarms 36 may be initiated. Such alarms may be aural or visual or both.

As will be seen from the above discussion, the pump 14 provides for a flow of fluid at a controlled rate from the source 10 to the patient. However, the pressure of the fluid flowing to the patient is at a relatively low level dependent upon the positioning of the source 10 above the pump 14. This may be seen from the fact that the operation of the pump is discontinued when the pressure of the fluid on the output line 16 rises above the pressure of the fluid on the input line. The pressure of the fluid in the output line 16 may be adjusted to any low value desired by adjusting the height of the source 10 above the pump 14. This is important when such patients as babies are receiving the intravenous fluid because babies can be injured when intravenous fluid at relatively high pressures is introduced to them.

The apparatus constituting this invention has other advantages. For example, whenever an obstruction occurs, the apparatus of this invention operates in fail-safe manner to insure that the pump 14 will become idled. The discontinuance in the operation of the pump results from the gravitational effects in providing particular fluid pressures at different positions in the apparatus. By disposing the sensor 26 at a position slightly above the output line, the pump 14 can be idled when the pressure of the fluid in the output line has a relatively low pressure such as one (1) pound per square inch (psi). This insures that the system is responsive to low pressures even when the pump 14 operates at high pressures. As previously explained, this is particularly important when fluids are introduced by the system to infants.

In addition to the advantages discussed above, the bypass line 20 offers certain other advantages of some importance. For example, the bypass line operates to trap air bubbles and thereby prevent such bubbles from passing to a patient. The passage of air bubbles to a patient is dangerous because the bubbles enter the blood vessels of the patient and block the passage of blood through these vessels. The trapping of fluid in the bypass lines results in part from the series relationship provided by the input line 12, the implementing means and the output line 16 and the connection of the bypass means in a parallel relationship across the implementing means.

The trapping of air bubbles is also facilitated by the disposition of a hydrophilic membrane 40 across the bypass line 20 at the juncture with the input line 12 and the disposition of a hydrophilic membrane 42 across the bypass line 20 at the juncture with the output line 16. The hydrophilic membranes 40 and 42 may be constructed in a conventional manner.

The hydrophilic membrane 40 provides for the passage of liquid from the input line 12 to the bypass line 20 but prevents air bubbles from passing from the bypass line to the input line 16. This is particularly important because air bubbles may otherwise be sucked into the input line when the piston in the pump 14 moves downwardly and tends to create a vacuum in the pump. Since air bubbles passing to a patient can provide serious injury to a patient in limiting blood flow through the patient, the trapping of air bubbles in the bypass line by the membrane 40 provides a distinct advantage in the operation of the system.

Similarly, the membrane 42 provides for a passage of liquid from the output line 16 to the bypass line 20 but prevents air bubbles from flowing from the bypass line to the output line. This is also instrumental in insuring that air bubbles cannot flow to the patient.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination for introducing fluid to a patient,
flow lines for providing a flow of fluid on a gravitational basis, the flow lines including an input line and an output line,
implementing means having an input for receiving fluid from the input flow line and having an output for directing fluid into the output flow line and disposed between the input and output flow lines and constructed and operative to pump fluid through the input and output flow lines, means disposed in a parallel relationship with the implementing means between the input and output lines and including means for establishing a fluid-isolated relationship between the input and the output of the implementing means and for alleviating the pressure in the output line, means associated with the flow lines and operatively associated with the parallel means at the end of the parallel means communicating with output line for sensing an obstruction at a relatively low pressure in the output line in accordance with the pressure of the fluid in the output line, and means responsive to the sensing means for discontinuing the operation of the implementing means when the sensing means senses an obstruction at a relatively low pressure in the output flow line.

2. The combination set forth in claim 1 wherein a source of fluid is provided and the flow lines are disposed to receive the fluid from the source and to pass the fluid to the patient and are disposed relative to the source to provide a build-up in pressure from the source and the sensing means are disposed in the parallel means relative to the flow lines to sense when the pressure of the fluid flowing to the patient increases to a value above the built-up pressure in the flow lines and wherein the parallel means are disposed relative to the input and output lines to trap air in the input line and prevent such air from passing into the output line.

3. In combination for introducing fluid to a patient, a source of fluid,
an input conduit extending from the source to a first position,
pump means connected to the input conduit at the first position to pump fluid through the input conduit at a controlled rate,
an output conduit extending from the pump means to a second position below the first position,
means disposed in parallel with the pump between the input and output conduits, such parallel means including means for establishing a fluid-isolated relationship between the input and output conduits and for alleviating the pressure in the output line, and
means operatively associated with the parallel means for detecting pressures of the fluid in the output conduit above the pressures produced in the fluid by the differences in height between the first and second positions to control the further operation of the pump means.

4. The combination set forth in claim 3, including,
means responsive to the detection of fluid pressures in the output conduit above the pressures of the fluid at the first position for interrupting the operation of the pump in introducing fluid to the output conduit,
the parallel means being constructed to entrap air in the input conduit and prevent such air from passing to the output conduit.

5. In combination for introducing fluid to a patient, a source of fluid,
an input line extending from the source to a first position,
an output line extending downwardly for connection to the patient,
implementing means connected at the first position to the input and output lines to pump the fluid from the source to the patient at a particular rate,
bypass means disposed between the input and output lines and operative to entrap air in the input line and prevent such air from passing to the output line, and
the bypass means including means for providing a fluid-isolated relationship between the input and output lines and for alleviating the fluid pressure in the output line, and
sensing means operatively associated with the bypass means to detect the pressure of the fluid in the output line and to interrupt the operation of the implementing means when the pressure of the fluid has risen to a value dependent upon the difference in height between the first position and the position of connection of the output line to the patient.

6. The combination set forth in claim 5, including,
switching means having open and closed states and operatively associated with the sensing means to become opened when the sensing means senses a pressure of the fluid in the output line at the particular level, the switching means being connected in a circuit with the implementing means to discontinue the operation of the implementing means.

7. The combination set forth in claim 6 wherein the implementing means constitutes a pump.

8. In combination for introducing fluid to a patient, a source of fluid,
an input line extending from the source and disposed below the source to provide a particular pressure of the fluid from the source in accordance with the vertical distance of the input line below the source,
an output line extending downwardly to the patient,
implementing means connected to the input and output lines to pump fluid from the source to the patient at a particular rate,
sensing means operatively associated with the output line to detect the pressure of the fluid in the output line and to interrupt the operation of the implementing means when the pressure of the fluid has risen to at least the particular pressure,
switching means having open and closed states and operatively associated with the sensing means to become opened when the sensing means senses a pressure of the fluid in the output line at the particular level, the switching means being connected in a circuit with the implementing means to discontinue the operation of the implementing means,
the implementing means constituting a pump,
a bypass line connected across the implementing means and communicating with the input and output lines,
resilient means disposed in the bypass line to isolate the input side of the bypass line against the flow of fluid to the output side of the bypass line and to alleviate the pressure of the fluid in the output line, and
the sensing means being disposed at a particular position at the output side of the bypass line to sense the presence of fluid at this particular position in the bypass line and to provide for the opening of the switching means upon such a fluid pressure.

9. In combination for introducing fluid from a source to a patient, flow lines for providing a flow of fluid on a gravitational basis, means disposed in the flow lines and operative to implement a flow of fluid through the flow lines, means associated with the flow lines for sensing an obstruction in the flow lines or an improper operation of the implementing means in accordance with the pressure of the fluid in the flow lines, and means responsive to the sensing means for discontinuing the operation of the implementing means when the sensing means senses an obstruction in the flow lines or an improper operation of the implementing means, the flow lines being disposed to receive the fluid from the source and to pass the fluid to the patient and being disposed relative to the source to provide a build-up in pressure from the source and the sensing means being disposed relative to the flow lines to sense when the pressure of the fluid flowing to the patient increases to a value above the built-up pressure in the flow lines, the flow lines and the implementing means being connected in a series relationship and a bypass line being connected in a parallel relationship with the implementing means and means being included in the bypass line to inhibit the flow of fluid through the bypass line and the sensing means being disposed to sense the pressure of the fluid in the bypass line, hydrophilic membrane means being disposed between the flow lines and the bypass line to provide for a passage of liquid from the flow lines to the bypass line and to prevent a passage of air bubbles from the bypass line to the flow lines.

10. In combination for introducing fluid from a source to a patient, flow lines for providing a flow of fluid on a gravitational basis, means disposed in the flow lines and operative to implement a flow of fluid through the flow lines, means associated with the flow lines for sensing an obstruction in the flow lines or an improper operation of the implementing means in accordance with the pressure of the fluid in the flow lines, and means responsive to the sensing means for discontinuing the operation of the implementing means when the sensing means senses an obstruction in the flow lines or an improper operation of the implementing means, the flow lines being disposed to receive the fluid from the source and to pass the fluid to the patient and being disposed relative to the source to provide a build-up in pressure from the source and the sensing means being disposed relative to the flow lines to sense when the pressure of the fluid flowing to the patient increases to a value above the built-up pressure in the flow lines, the flow lines and the implementing means being connected in a series relationship and a bypass line being connected in a parallel relationship with the implementing means and means being included in the bypass line to inhibit the flow of fluid through the bypass line and the sensing means being disposed to sense the pressure of the fluid in the bypass line, first hydrophilic membrane means being disposed between the input conduit and the bypass line to provide for a passage of liquid from the input conduit to the bypass line and to prevent a passage of air bubbles from the bypass line to the input conduit, and second hydrophilic membrane means being disposed between the output conduit and the bypass line to provide for a passage of liquid from the output conduit to the bypass line and to prevent a passage of air bubbles from the bypass line to the output conduit.

11. In combination for introducing fluid to a patient, a source of fluid, an input line extending from the source and disposed below the source to provide a particular pressure of the fluid from the source in accordance with the vertical distance of the input line below the source, an output line extending downwardly to the patient, implementing means connected to the input and output lines to implement the flow of fluid from the source to the patient at a particular rate, sensing means operatively associated with the output line to detect the pressure of the fluid in the output line and to interrupt the operation of the implementing means when the pressure of the fluid has risen to at least the particular pressure, switching means having open and closed states and operatively associated with the sensing means to become opened when the sensing means senses a pressure of the fluid in the output line at the particular level, the switching means being connected in a circuit with the implementing means to discontinue the operation of the implementing means, the implementing means constituting a pump, a bypass line connected across the implementing means, means disposed in the bypass line to isolate the input side of the bypass line against the flow of fluid to the output side of the bypass line, and the sensing means being disposed at a particular position at the output side of the bypass line to sense the presence of the fluid at this particular position in the bypass line and to provide for the opening of the switching means upon such a fluid pressure, first means providing a hydrophilic action in providing for a passage of liquid from the input line to the bypass line and in preventing a passage of air bubbles from the bypass line to the input line, and second means providing a hydrophilic action in providing for a passage of liquid from the output line to the bypass line and in preventing a passage of air bubbles from the bypass line to the output line.

12. In combination for introducing fluid from a source to a patient, flow lines for providing a flow of fluid on a gravitational basis, implementing means disposed in the flow lines and operative to pump fluid through the flow lines, means associated with the flow lines for sensing an obstruction in the flow lines or an improper operation of the implementing means in accordance with the pressure of the fluid in the flow lines, and means responsive to the sensing means for discontinuing the operation of the implementing means when the sensing means senses an obstruction in the flow lines or an improper operation of the implementing means, the flow lines being disposed to receive the fluid from the source and to pass the fluid to the patient and being disposed relative to the flow lines to sense when the pressure of the fluid flowing to the patient increases to a value above the built-up pressure in the flow lines,
the flow lines and the implementing means being connected in a series relationship and a bypass line being connected in a parallel relationship with the implementing means between the flow lines and being constructed to entrap air in the flow lines and means being included in the bypass line to prevent the flow of fluid through the bypass line and to alleviate the pressure of the fluid in the input line, the sensing means being disposed to sense the pressure of the fluid in the bypass line.

13. The combination set forth in claim 12 wherein the sensing means is disposed on the output side of the bypass line to sense the pressure of the fluid passing to the patient and the implementing means constitutes a pump and the means included in the output line are resilient.

14. The combination set forth in claim 13 wherein the flow lines include an input line and an output line and the pump is connected to the output end of the input line and the input end of the output line and the bypass line is connected to the output end of the input line and the input end of the output line and the sensing means is responsive to the pressure of the fluid at the output end of the bypass line.

15. In combination for introducing fluid to a patient, a source of fluid,
an input conduit extending from the source to a first position,
a pump connected to the input conduit at the first position to pump fluid from the conduit to a controlled rate,
an output conduit extending from the pump to a second position below the first position,
means for detecting pressures of the fluid in the output conduit,
means responsive to the detection of fluid pressures in the output conduit for interrupting the operation of the pump in introducing fluid to the output conduit when the pressure in the output conduit exceeds a pressure dependent upon the difference in height between the first and second positions,
a bypass line extending between the input and output conduits in bypass relationship to the pump,
a chamber disposed in the bypass line and a resilient diaphragm extended across the chamber to prevent the flow of fluid through the bypass line and to alleviate the fluid pressure in the output line, and
the detecting means being disposed in operatively coupled relationship to the bypass line to detect the pressures of fluid in the output conduit.

16. The combination set forth in claim 8 wherein the implementing means is a pump and
the isolating means is a chamber and a diaphragm extending across the chamber.

* * * * *